United States Patent
Motta

(10) Patent No.: US 9,010,853 B2
(45) Date of Patent: Apr. 21, 2015

(54) SECURING ELEMENT, PARTICULARLY SUITABLE FOR USE WITH TABLET-ARM CHAIRS

(75) Inventor: Alberto Lievore Motta, Irun (ES)

(73) Assignee: Sellex, S.A., Irun (Guipuzcoa) (ES)

( * ) Notice: Subject to any disclaimer, the term of this patent is extended or adjusted under 35 U.S.C. 154(b) by 54 days.

(21) Appl. No.: 13/880,750

(22) PCT Filed: Oct. 19, 2011

(86) PCT No.: PCT/ES2011/070722
§ 371 (c)(1),
(2), (4) Date: Jun. 28, 2013

(87) PCT Pub. No.: WO2012/052591
PCT Pub. Date: Apr. 26, 2012

(65) Prior Publication Data
US 2013/0270873 A1    Oct. 17, 2013

(30) Foreign Application Priority Data

Oct. 22, 2010 (ES) .................. 201031052 U

(51) Int. Cl.
| | |
|---|---|
| A47C 7/70 | (2006.01) |
| C07D 205/08 | (2006.01) |
| C07D 263/20 | (2006.01) |
| A47B 83/02 | (2006.01) |

(52) U.S. Cl.
CPC .............. *A47C 7/70* (2013.01); *C07D 205/08* (2013.01); *C07D 263/20* (2013.01); *A47B 83/02* (2013.01)

(58) Field of Classification Search
USPC ........ 297/135, 160, 170, 173, 174 R, 188.17, 297/188.2; 248/229.1, 229.13; 403/385, 403/389, 391, 395
See application file for complete search history.

(56) References Cited

U.S. PATENT DOCUMENTS

| | | | | |
|---|---|---|---|---|
| 935,730 | A | * | 10/1909 | Bacon ........................ 248/207 |
| 1,364,053 | A | * | 12/1920 | Quintin ................... 248/229.11 |
| 2,452,406 | A | * | 10/1948 | Volkery et al. ............... 403/391 |
| 3,521,332 | A | * | 7/1970 | Kramer ........................ 403/188 |
| 4,190,224 | A | * | 2/1980 | LeBlanc et al. ............. 248/227.3 |
| 4,711,422 | A | * | 12/1987 | Ibanez ........................ 248/515 |
| 4,779,884 | A | | 10/1988 | Minati |
| D320,548 | S | * | 10/1991 | Blatt ............................ D8/396 |
| 6,375,257 | B1 | | 4/2002 | Wooding et al. |
| 6,505,825 | B1 | * | 1/2003 | Hurst et al. ..................... 269/71 |
| 6,899,386 | B2 | * | 5/2005 | Anton ....................... 297/174 R |
| 6,966,086 | B2 | * | 11/2005 | Metz et al. .................... 248/121 |
| 7,900,566 | B1 | * | 3/2011 | Bunker ........................ 297/170 |
| 2004/0004372 | A1 | | 1/2004 | Mullen et al. |
| 2004/0206277 | A1 | | 10/2004 | Roziere |

* cited by examiner

FOREIGN PATENT DOCUMENTS

CA        2515709 A1    2/2006

*Primary Examiner* — Peter Brown
(74) *Attorney, Agent, or Firm* — Hayes Soloway PC

(57) ABSTRACT

The invention can be used to secure writing tablets to different types of chairs with legs of different thicknesses and diameters, such that writing tablets can be installed on simple chairs with no armrests. The invention is essentially characterized in that it comprises: a main part having two through-holes therein, namely a first hole for receiving and housing the tubular support of the writing tablet and a second hole dimensioned to be coupled to one of the legs of the chair, and a vertical rod; and a pivoting part connected to the main part by means of the rod, aligned with the second hole and adapted to open and close such that the securing element can be released from the leg of the chair.

5 Claims, 4 Drawing Sheets

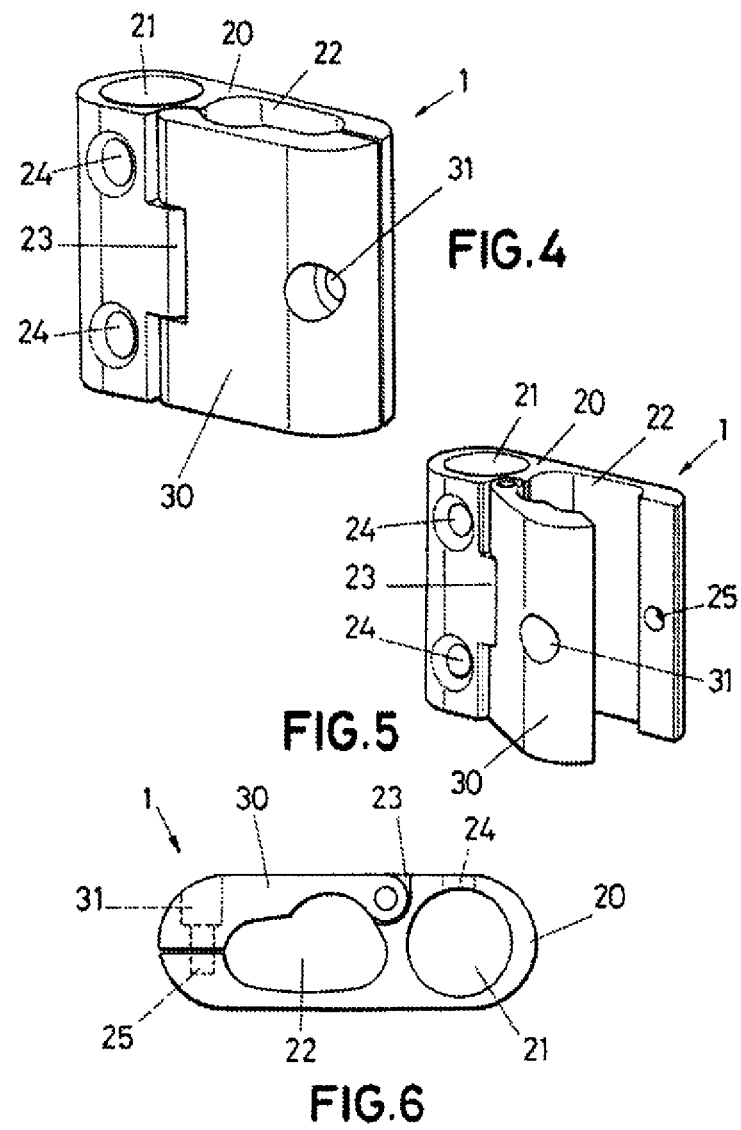

SECURING ELEMENT, PARTICULARLY SUITABLE FOR USE WITH TABLET-ARM CHAIRS

OBJECT OF THE INVENTION

The present invention belongs to the field of chairs and, more specifically, to accessories and components for chair desks, of the type comprising a writing tablet.

The main object of the present invention is a securing element especially intended for chair desks, whereby a means for joining and securing one of the chair legs to the writing tablet itself is established.

BACKGROUND OF THE INVENTION

Chair desks generally used in meetings, congresses, conferences, courses or similar are known in the current state of the art. This type of chair desk arises from the need for a support on which to write and handle documents, providing a document holder or tablet, preferably ergonomic and pivoting, which is generally incorporated in the right armrest of the chair or seat.

In general, said writing tablets are articulately mounted, determining a rotation between a horizontal use position and a vertical perpendicular pivoted position, allowing the user to easily sit down and get up from the chair.

Current drawbacks of chair desks include the following, among others:

- The writing tablet is mounted on one of the chair's armrests, not allowing use thereof in chairs having simple structures without said armrests.
- Mounting of the writing tablet on the tablet is permanent and complex, which considerably limits the use possibilities of the chair in question.
- Fixation of said writing tablets is limited to a certain type of chairs having specific dimensions and thicknesses.

DESCRIPTION OF THE INVENTION

The present invention resolves all of the aforementioned drawbacks by providing a securing element, especially applicable to chair desks, which allows fixation of writing tablets to different types of chairs having legs of different thicknesses and diameters, enabling installation thereof in chairs having simple structures without armrests, said securing element being adapted for simple, fast and safe assembly and disassembly on one of the chair legs.

The securing element object of the invention is especially intended for chair desks comprising a writing tablet having a tubular support underneath for joining and securing thereof to the chair.

Said securing element comprises a main part having two pass-through openings in its interior: a first opening destined to receive and house the tubular support of the writing tablet; and a second opening dimensionally adapted to allow coupling of the securing element described herein to one of the chair legs, preferably the front right leg, regardless of the perimeter, thickness or diameter of said leg.

To this end, the main part comprises a vertical rod, preferably located in the centre thereof, between the two aforementioned openings, whereto a pivoting part coincident with the second opening is associated and adapted to open and close, enabling the release of the securing element in relation to the chair leg.

In accordance with a preferred embodiment of the invention, the main part and pivoting part are associated by means of vertical nipples disposed on either side of the rod, which are destined to be inserted into longitudinal bores in the pivoting part. Said bores can be fully pass-through to the end of the pivoting part or only partially pass-through for exclusively disposing the rod nipples.

In accordance with another preferred embodiment, the main part and pivoting part are associated by means of a longitudinal axis that crosses both the rod of the main part and the pass-through bores of the pivoting part.

Preferably, both the main part and the pivoting part comprise at least one orifice wherein screwing means for firm and secure fixing thereof to the tubular part and to the chair leg, respectively, are destined to be inserted. Likewise, the securing element object of the invention will preferably have a cylindrical and flattened configuration, similar to the shape of a "hip flask", with curved sides without sharp edges, thereby avoiding possible injuries and tears in the user's leg.

DESCRIPTION OF THE DRAWINGS

In order to complete the description being made and with the object of helping to better understand the characteristics of the invention, in accordance with a preferred example of practical embodiment thereof, accompanying said description as an integral part thereof, is a set of drawings wherein the following has been represented in an illustrative and non-limiting manner:

FIG. 4 shows a perspective view of the securing element object of the invention.

FIG. 5 shows a perspective view of the securing element, where the partially folded cover corresponding to the chair leg can be observed.

FIG. 6 shows a top plan view of the securing element object of the invention where the special configuration of its two openings can be observed.

PREFERRED EMBODIMENT OF THE INVENTION

Figure 1:
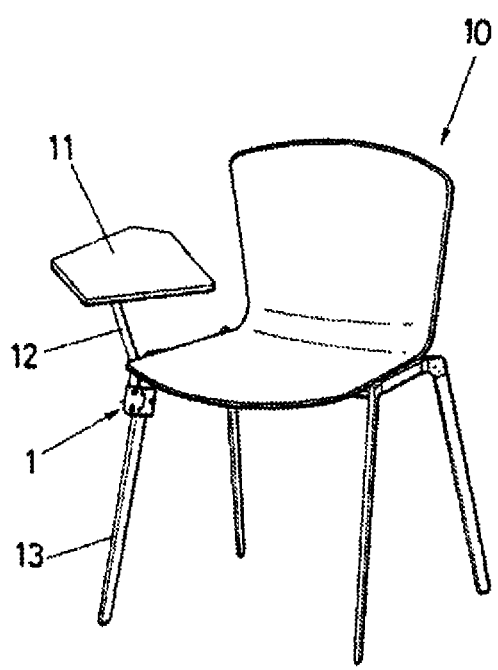
FIG. 1 shows a general perspective view of a chair desk that includes the securing element object of the invention.

FIG. 1 shows a chair desk (10) having a simple configuration without armrests, which comprises a horizontal writing tablet (11) having a tubular support (12) on its underside associated and secured to the front chair leg (13) by means of the securing element (1) object of the invention.

As can be observed in FIGS. 4, 5 and 6, said securing element (1) comprises:

- a main part (20) having two pass-through openings (21, 22) in its interior, a first opening (21) destined to receive and house the tubular support (12) of the writing tablet (11); and a second opening (22) dimensionally adapted for coupling to one of the chair legs (13), also comprising a vertical rod (23) disposed in the centre of the main part (20) between the two openings (21, 22), and
- a pivoting part (30) associated to the main part (20) through its rod (23), disposed coincident with the second opening (22), and adapted for opening and closing to enable the release of the securing element (1) in relation to the chair leg (13).

Figure 2:
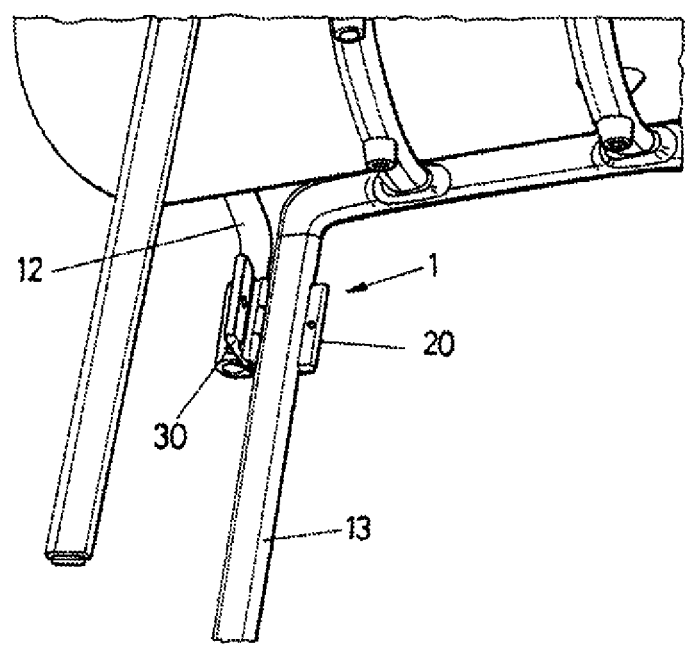
FIG. 2 shows a lower perspective view of a chair, where the joint between the securing element of the invention and the front right leg of the chair can be observed.

FIG. 2 shows a lower view of a chair desk (10) that includes the securing element (1) of the present invention, installed on the front right leg (13) thereof. In said FIG. 2 the pivoting part (30) is represented in its open position, showing the special configuration of the chair leg (13), which has a longitudinal recess on one of its sides. Nevertheless, despite the different perimeters and reliefs of the leg (13), the securing element (1) is firmly secured and fixed by means of screwing means (40) inserted in orifices (24, 25, 31) in both the main part (20) and the pivoting part (30) destined for such purpose.

Figure 3:
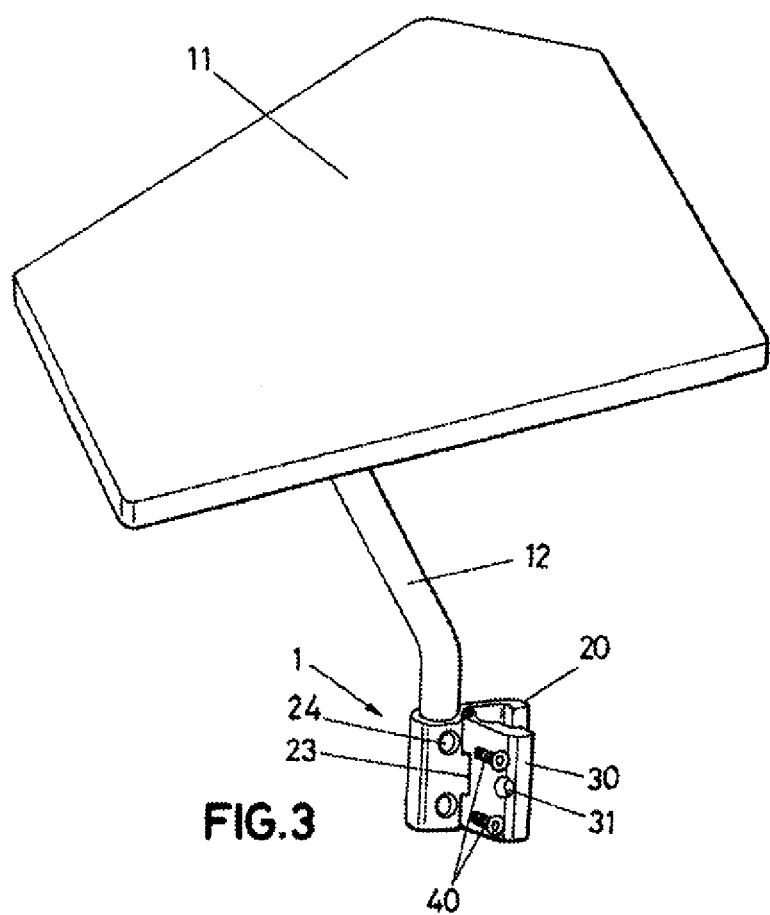
FIG. 3 shows a view of the joint between the tubular support of the writing tablet and the securing element object of the invention.

Said screwing means (40) can be observed in FIG. 3. In accordance with the present embodiment, the main part (20) comprises two primary orifices (24) for securing the securing element (1) to the tubular support (12) and a secondary orifice (25) for securing the securing element (1) to the chair leg (13).

For its part, the pivoting part (30) comprises a third orifice (31) destined to be disposed coincident with the secondary orifice (25) of the main part (20).

As can be observed in FIG. 6, the securing element (1) described herein basically stands out for being adapted for coupling to legs (13) of different diameters and configurations.

Said FIG. 6 shows the first opening (21) with a circular configuration, whereinto the tubular support (12) of the writing tablet (11) is destined to be inserted. On the other hand, the second opening (22), whereinto the chair leg (13) is destined to be inserted, has an irregular and asymmetrical configuration, where the area of the opening (22) corresponding to the perimeter edge of the main part (20) has an ellipse-like configuration; and the area of the opening (22) in correspondence with part of the perimeter edge of the pivoting part (30) has an asymmetrical configuration, with an oval-shaped double recess in the closed position of said pivoting part (30).

The invention claimed is:

1. A securing element, particularly applicable to desk-chairs having:
   a chair;
   chair legs located on the chair, and
   a writing tablet having a tubular support at a lower part thereof for joining and fastening the writing tablet to the chair,
   said securing element comprising:
   a main part,
   a first through opening formed in the main part, for receiving and housing the tubular support of the writing tablet,
   a second through opening, formed in the main part, and dimensionally adapted for coupling to one of the chair legs,
   at least one primary hole on the main part, communicating with the first through opening, for fastening the tubular support in the first through opening of the main part,
   a secondary hole on the main part,
   a pivoting part associated with the main part, and
   a vertical rod, for pivotally associating the pivoting part to the main part, so as to allow the pivoting part being opened and closed, for allowing to switch from a closed position in which the pivoting part clamps the chair leg, to a opened position in which the pivoting part is released from the chair leg to thereby allowing release of the securing element with respect to the chair leg,
   wherein the pivoting part further comprises a third hole positioned so as to be collinear to the secondary hole when the pivoting part is in the closed position, for fastening the chair leg to the securing element,
   wherein the pivoting part has a perimetral edge, the second opening having an asymmetrical shape, in correspondence with part of the perimetral edge of the pivoting part, with a double oval-shaped recess in the closed position of said pivoting part, for better fitting chair legs having different shapes.

2. The securing element of claim 1, further comprising screwing means for being inserted in the primary hole, secondary hole and third hole for securing the main part and the pivoting part to the tubular support of the writing tablet and to the chair leg, respectively.

3. The securing element of claim 1, wherein the main part has a central area, the vertical rod being located in the central area of the main part and between the first opening and the second opening.

4. The securing element of claim 1, having a parallelepipedical shape with rounded edges.

5. The securing element of claim 1, wherein the first opening has a circular shape.

* * * * *